US008067034B2

(12) United States Patent
Moriyama et al.

(10) Patent No.: US 8,067,034 B2
(45) Date of Patent: Nov. 29, 2011

(54) FUNCTIONAL FOOD FOR AMELIORATING ENDOGENOUS MELATONIN SECRETION RHYTHM AND FUNCTIONAL FOOD FOR AMELIORATING CIRCADIAN RHYTHM

(75) Inventors: Yoshinori Moriyama, Okayama (JP); Seiji Tsuboi, Okayama (JP); Akihiro Masuyama, Sagamihara (JP); Toshiaki Takano, Kawasaki (JP); Keita Ueno, Tokyo (JP); Toshiyuki Kai, Machida (JP)

(73) Assignee: CALPIS Co., Ltd, Tokyo (JP)

( * ) Notice: Subject to any disclaimer, the term of this patent is extended or adjusted under 35 U.S.C. 154(b) by 0 days.

(21) Appl. No.: 11/952,839

(22) Filed: Dec. 7, 2007

(65) Prior Publication Data
US 2008/0268065 A1    Oct. 30, 2008

Related U.S. Application Data

(63) Continuation of application No. 10/599,446, filed as application No. PCT/JP2005/006244 on Mar. 31, 2004, now abandoned.

(30) Foreign Application Priority Data

Mar. 31, 2004 (JP) .................................. 2004-106153
Jun. 4, 2004 (JP) .................................. 2004-166498

(51) Int. Cl.
*A61K 35/20* (2006.01)
(52) U.S. Cl. ...................................... 424/535; 424/115
(58) Field of Classification Search .................. None
See application file for complete search history.

(56) References Cited

U.S. PATENT DOCUMENTS

| 5,449,683 | A | 9/1995 | Wurtman |
| 6,235,719 | B1 | 5/2001 | Harang |
| 6,284,243 | B1 | 9/2001 | Masuyama et al. |
| 6,444,203 | B2 | 9/2002 | Kreuger et al. |
| 6,534,304 | B1 | 3/2003 | Yamamoto et al. |
| 6,900,180 | B1 * | 5/2005 | Hageman et al. ............... 514/23 |
| 2004/0097714 | A1 | 5/2004 | Maubois et al. |
| 2005/0074500 | A1 | 4/2005 | Kitamura et al. |

FOREIGN PATENT DOCUMENTS

DE   94 11 450 U1   10/1994
EP   0 357 162 A2   3/1990

OTHER PUBLICATIONS

Kajimoto et al., Journal of Nutritional Food, 2001, vol. 4 No. 3, p. 51-61.*
Dijk et al., Journal of Physiology, 1997, vol. 505, No. 3, p. 851-858.*
Matar et al., Int. Dairy Journal, 1996, vol. 6, p. 383-397.*
Clare et al., J Dairy Sci, 2000 vol. 83, p. 1187-1195.*
Seiji Tsuboi et al; "Hakkonyu Whey Toyo ni yoru Rat Shokataichu Melatoniin Gosei eno Eikyo", Nippon Yakugakukai Nenkai Keon Yoshishu, Mar. 5, 2005, vol. 125, No. 3, p. 4330-0148.
Heine, W. et al., "The Significance of Trypotophan in Human Nutrition" Amino Acid, (1995), vol. 9, pp. 191 to 195, full text Summary, Fig 1, p. 200, 10th line from the bottom of p. 201, line 26.
Cardinali D P et al.: "Melatonin in Sleep Disorders and Jet-Lag" Neuro Endocrinology Letters, Weinheim, DE, vol. 23, No. Suppl. 01, Jul. 1, 2002, pp. 9-13, XP008025315.

* cited by examiner

*Primary Examiner* — Kade Ariani
(74) *Attorney, Agent, or Firm* — Sughrue Mion, PLLC

(57) ABSTRACT

Disclosed are agents for phase-adjusting or enhancing the amplitude of an endogenous melatonin secretion rhythm and for improving a circadian rhythm, as well as functional food containing such an agent, which may prevent or ameliorate various symptoms, such as sleep disorder or prolonged sleep latency. The agent contains whey as the active component.

4 Claims, 2 Drawing Sheets

FUNCTIONAL FOOD FOR AMELIORATING ENDOGENOUS MELATONIN SECRETION RHYTHM AND FUNCTIONAL FOOD FOR AMELIORATING CIRCADIAN RHYTHM

This is a continuation of application Ser. No. 10/599,446 filed Feb. 8, 2007, now abandoned which is a 371 of PCT/JP2005/006244 claiming the benefit Japanese Patent Applications 2004-106156 filed Mar. 31, 2004 and 2004-166498 filed Jun. 4, 2004, the entire disclosures of these prior applications being considered part of the disclosure of the accompanying application number they are hereby incorporated by reference.

FIELD OF ART

The present invention relates to functional food for improving an endogenous melatonin secretion rhythm and functional food for improving a circadian rhythm, which are expected to prevent or ameliorate sleep disorder or prolonged sleep latency, a material for the active component of such food, and an agent for phase-adjusting or enhancing the amplitude of an endogenous melatonin secretion rhythm and an agent for improving a circadian rhythm, which may prevent or ameliorate various disorders associated with disorders of the endogenous melatonin secretion rhythm or the circadian rhythm.

BACKGROUND ART

People in the modern world tend to lead irregular lifestyle under the influence of recent advances and complication of technologies as well as fast-moving social situation. The advent of the 24-hour society has forced people into an irregular mode of life, which leads to circadian rhythm disorder, such as sleep disorder, or disorder of an endogenous melatonin secretion rhythm, which is a possible factor for the circadian rhythm disorder.

It has been confirmed that entrainment of a circadian rhythm is controlled in the suprachiasmatic nucleus (SCN) in the hypothalamus. A typical substance that is known to regulate a circadian rhythm controlled by the suprachiasmatic nucleus is melatonin (N-acetyl-5-methoxytryptamine) secreted mainly from the corpus pineale. Melatonin is a hormone synthesized from tryptophan through serotonin under the action of NAT (N-acetyltransferase) as a rate-limiting enzyme. This hormone is believed to be involved in introduction of photoperiodic information in photoperiodic mammals and exert an influence on reproduction, body weight, metabolic regulation, circadian rhythm control, as well as nervous and endocrine functions. Further, since the melatonin secretion level of the corpus pineale is low in the day time and high in the night time, melatonin is believed to be one of the sleep-modulatory substances.

It is known that the melatonin secretion rhythm in patients with sleep disorder or circadian rhythm disorder is different from that of healthy people in that the amplitude is decreased or the phase is either advanced or delayed.

For overcoming such disorders of a circadian rhythm or a melatonin secretion rhythm to treat or prevent sleep disorder, administration of exogenous melatonin has been proposed. For example, Patent Publication 1 reports that oral administration of melatonin from an external source to artificially regulate a melatonin rhythm has an effect on non-24-hour sleep-wake syndrome, jet lag syndrome, shift-work sleep syndrome, delayed sleep phase syndrome, or the like, accompanied by prolonged sleep latency, insomnia, waking in bad mood, jet lag, reverse of day and night, or the like.

However, the safety of melatonin products, including the side effect of exogenous melatonin products per se, has not been fully assured.

Patent Publication 2 proposes a composition for improving the quality of sleep, containing as the active component muramyl peptide prepared by hydrolysis from the cell wall of non-pathogenic lactic acid bacteria. However, the improvement in the quality of sleep taught in this publication is achieved by increasing the length of the non-REM sleep phase through induction of sleep by the immune system, so that this way of improving the quality of sleep is completely different from the improvement of the endogenous melatonin secretion level.

Patent Publication 1: JP-08-502259-T
Patent Publication 2: JP-2003-517828-T

SUMMARY OF THE INVENTION

It is an object of the present invention to provide an agent for phase-adjusting or enhancing the amplitude of an endogenous melatonin secretion rhythm and an agent for improving a circadian rhythm, which may be taken daily and continuously, have excellent safety, and may effectively prevent or ameliorate disorders of an endogenous melatonin secretion rhythm or of a circadian rhythm without administration of exogenous melatonin.

It is another object of the present invention to provide functional food, such as foods for specified health uses, which may be taken daily and continuously, has excellent safety, and may effectively prevent or ameliorate various disorders including sleep disorder or prolonged sleep latency possibly caused by disorders of an endogenous melatonin secretion rhythm or of a circadian rhythm, without administration of exogenous melatonin.

According to the present invention, there is provided an agent for phase-adjusting or enhancing an amplitude of an endogenous melatonin secretion rhythm comprising whey as an active component.

According to the present invention, there is also provided an agent for improving a circadian rhythm comprising whey as an active component.

According to the present invention, there is further provided functional food for improving an endogenous melatonin secretion rhythm, such as preventing or ameliorating sleep disorder or prolonged sleep latency, comprising the above-mentioned agent for phase-adjusting or enhancing an amplitude of an endogenous melatonin secretion rhythm.

According to the present invention, there is also provided functional food for improving a circadian rhythm, such as preventing or ameliorating sleep disorder or prolonged sleep latency, comprising the above-mentioned agent for improving a circadian rhythm.

According to the present invention, there is provided a method for phase-adjusting or enhancing an amplitude of an endogenous melatonin secretion rhythm comprising the step of orally administering to an animal in need thereof an effective amount of an agent for phase-adjusting or enhancing an amplitude of an endogenous melatonin secretion rhythm comprising whey as an active component.

According to the present invention, there is also provided a method for improving a circadian rhythm comprising the step of orally administering to an animal in need thereof an effective amount of an agent for improving a circadian rhythm comprising whey as an active component.

According to the present invention, there is further provided use of whey for the manufacture of an agent for phase-adjusting or enhancing an amplitude of an endogenous melatonin secretion rhythm, or for the manufacture of functional food for phase-adjusting or enhancing an amplitude of an endogenous melatonin secretion rhythm.

According to the present invention, there is also provided use of whey for the manufacture of an agent for improving a circadian rhythm, or for the manufacture of functional food for improving a circadian rhythm.

Since the agent for phase-adjusting or enhancing the amplitude of an endogenous melatonin secretion rhythm, and the agent for improving a circadian rhythm according to the present invention contain whey, which has been taken as food, as the active component, the present agents may be taken daily and continuously, are excellently safe, and are expected to prevent or ameliorate sleep disorder or prolonged sleep latency, such as non-24-hour sleep-wake syndrome, jet lag syndrome, shift-work sleep syndrome, sleep apnea syndrome, and middle-age sleep disorder, which are believed to be associated with the disorders of such rhythms.

Since the functional food according to the present invention contains the agent for phase-adjusting or enhancing the amplitude of an endogenous melatonin secretion rhythm or the agent for improving a circadian rhythm of the present invention, the present functional food may prevent or ameliorate various symptoms such as sleep disorder or prolonged sleep latency, without administration of exogenous melatonin.

PREFERRED EMBODIMENTS OF THE INVENTION

Figure 1:
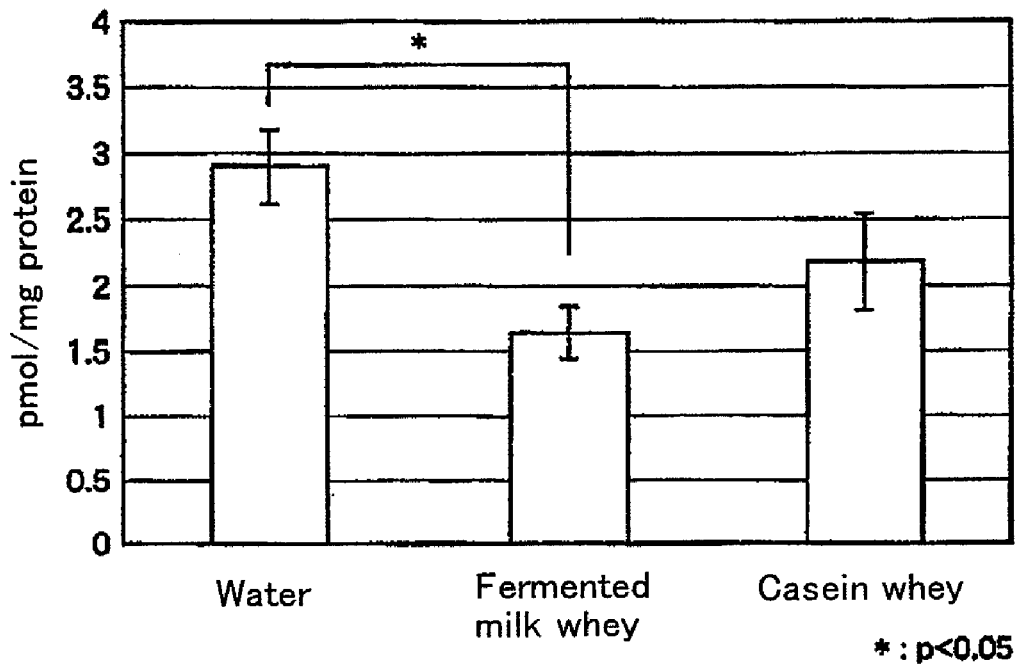
FIG. 1 is a graph illustrating the comparison among the groups of the melatonin concentration in the corpus pineale at 12:00 performed in Examples 1 and 2.

The present invention will now be explained in detail.

The agent for phase-adjusting or enhancing the amplitude of an endogenous melatonin secretion rhythm according to the present invention is capable of preventing or ameliorating various disorders caused by disorder of an endogenous melatonin secretion rhythm, exhibits at least one of a phase-adjusting effect and an amplitude enhancing effect on the rhythm, and contains whey as the active component.

The agent for improving a circadian rhythm according to the present invention exhibits an effect of preventing or ameliorating various disorders caused by circadian rhythm disorder, and contains whey as the active component.

The active component, whey, includes an aqueous fraction of milk obtained by removing all or most of the casein protein and the like from milk according to a common procedure, and may be, for example, acid whey and/or cheese whey. Examples of the acid whey may include fermented milk whey obtained by fermentation of milk with lactic acid bacteria, and casein whey containing an aqueous fraction of milk obtained by adding acid to milk to remove all or most of the casein protein and the like according to a common procedure. Fermented milk whey is particularly preferred for its excellent ability to phase-adjust or enhance the amplitude of an endogenous melatonin secretion rhythm or to improve a circadian rhythm.

The fermented milk whey may usually be a fermented milk whey prepared by fermentation of milk with lactic acid bacteria, or by symbiotic fermentation of milk with lactic acid bacteria and a yeast. The starting material milk may be animal milk, such as cow's milk, goat's milk, or sheep's milk; vegetable milk, such as soy bean milk; or processed milk thereof, such as skim milk, reconstituted milk, powdered milk, or condensed milk. The milk may be in the form of a mixture.

The solid content of the milk is not particularly limited. For example, for skim milk, the solid non-fat content is typically about 9 mass %. On the other hand, considering the per-plant productivity, the solid non-fat content may be increased to some extent. The fermented milk whey obtained in the production of fermented milk may be separated from other milk components before use, but when the fermented milk whey is to be made into the functional food or the like to be discussed later, such other milk components are not necessarily separated.

The lactic acid bacteria may be those of the genus *Streptococcus, Lactococcus, Lactobacillus, Bifidobacterium*, or the like, with *Lactobacillus* being preferred. Specific examples of *Lactobacillus* may include *Lactobacillus bulgaricus, Lactobacillus helveticus, Lactobacillus casei, Lactobacillus acidophilus*, and *Lactobacillus fermentum*, with *Lactobacillus helveticus* being particularly preferred. More specifically, *Lactobacillus helveticus* ATCC 15009, *Lactobacillus helveticus* ATCC 521, and *Lactobacillus helveticus* CM4 strain (deposited at National Institute of Advanced Industrial Science and Technology, International Patent Organism Depositary under Accession Number FERM BP-6060 on Aug. 15, 1997) (referred to as CM4 hereinbelow) may be used, with CM4 being particularly preferred. CM4 has been deposited under the above-mentioned accession number under the Budapest Treaty on the International Recognition of the Deposit of Microorganisms for the Purposes of Patent Procedure. All restrictions on the availability to the public of this strain will be irrevocably removed upon the granting of a patent.

The lactic acid bacteria are preferably in the form of a pre-cultured starter having sufficiently high activity. The initial cell count may preferably be about $10^5$-$10^7$ cells/ml.

When the fermented milk whey is to be used in functional food, such as foods for specified health uses, yeast may be used for symbiotic fermentation for improved flavor and palatability. The strain of the yeast is not particularly limited, and may preferably be, for example, yeast of the genus *Saccharomyces*, such as *Saccharomyces cerevisiae*. The content of the yeast may suitably be selected depending on the purpose.

The fermentation may be carried out by culturing one or more kinds of the lactic acid bacteria in a medium, or culturing a mixture of one or more kinds of the lactic acid bacteria and one or more kinds of the yeast in a medium. The medium may be those composed only of one or more kinds of the milk components mentioned above, or those optionally contain additional components, such as yeast extract; vitamins, e.g. ascorbic acid; amino acids, e.g. cysteine; salts, e.g. sodium chloride; sugars, e.g. glucose, sucrose, raffinose, or stachyose; stabilizers, e.g. gelatine; and flavoring agents.

The fermentation may be performed usually by static or stirred culture, for example at 20 to 50° C., preferably 30 to 45° C., at the initial pH of 6.0 to 7.0, and may be terminated when the cell count becomes $10^7$ cells/ml or higher at pH 5.0 or lower. The milk may be subjected to high-temperature pasteurization before fermentation.

The fermented milk whey may be separated from curd by means of a common separating operation. On the other hand, when the fermented milk whey as the active component is to be used in the functional food to be discussed later, the fermented milk containing the whey may be used as it is without separation, if so desired, or the extent of separation may suitably be decided.

The casein whey may be prepared by, when solid milk, such as whole milk or skim milk is used, dissolving the milk in distilled water, adding, for example, lactic acid, citric acid, acetic acid, tartaric acid, fumaric acid, malic acid, gluconic acid, or adipic acid to adjust the acidity to a level suitable for removing protein, typically casein, and separating the whey component (aqueous fraction) by a common procedure, such as membrane filtration. Here, the milk may be subjected to high temperature pasteurization before the acid is added. The acid may usually be added in an amount for achieving 1.0 to 4.0% acidity, depending on the kind of the acid or the like.

The cheese whey may be prepared in the ordinary cheese production, by coagulating milk with rennet to form curd, and separating the whey component from the curd by centrifugation or the like. Here, the milk may be subjected to high temperature pasteurization before the rennet is added.

The dose of the sour milk whey as the active component in the agent for phase-adjusting or enhancing the amplitude of an endogenous melatonin secretion rhythm or in the agent for improving a circadian rhythm, is not particularly limited, taking the continuity of administration into account, and may usually be not less than 0.001 g per kg body weight per day, preferably not less than 0.01 g per kg body weight per day, in terms of freeze-dried powder. Further, the agent for phase-adjusting or enhancing the amplitude of an endogenous melatonin secretion rhythm or the agent for improving a circadian rhythm of the present invention may optionally contain components other than the whey as desired, having the function of phase-adjusting or enhancing the amplitude of an endogenous melatonin secretion rhythm or improving a circadian rhythm.

The agent for phase-adjusting or enhancing the amplitude of an endogenous melatonin secretion rhythm or the agent for improving a circadian rhythm according to the present invention may be in the form of whey with or without processing, for example, a whey concentrate obtained by concentrating whey through vacuum concentration or the like process, or a dried whey powder obtained by drying whey through freeze-drying or spray drying.

The agent for phase-adjusting or enhancing the amplitude of an endogenous melatonin secretion rhythm or the agent for improving a circadian rhythm according to the present invention may be administered usually through an oral route. For example, the agent may be administered even after the symptoms of sleep disorder caused by disorder of an endogenous melatonin secretion rhythm or of a circadian rhythm are developed, or in the seasons to prevent such symptoms, either continuously daily or intermittently.

The functional food for improving an endogenous melatonin secretion rhythm according to the present invention contains the agent for phase-adjusting or enhancing the amplitude of an endogenous melatonin secretion rhythm, and the functional food for improving a circadian rhythm according to the present invention contains the agent for improving a circadian rhythm.

The functional food may be functional food, such as foods for specified health uses, claiming prevention or amelioration of symptoms caused by disorder of an endogenous melatonin secretion rhythm or a circadian rhythm, such as prevention or amelioration of sleep disorder or prolonged sleep latency.

The functional food may optionally contain additives, such as sugars, proteins, lipids, vitamins, minerals, flavoring agents, or mixtures thereof. Further, the milk components from which the whey is separated, may also be contained.

In the functional food of the present invention, the content of the whey as the active component may suitably be selected depending on the form or kind of the food. The content may suitably be selected also depending on the continuity of intake of the functional food or the like factors, and is not particularly limited. A suitable content may be usually 1 to 100 mass %.

The various functional food mentioned above may be in the form of, for example, fermented milk products, such as yogurt or lactic acid bacteria beverage, processed food and beverage containing whey, dry powders, tablets, capsules, granules, or the like.

The dose and the timing of administration of the various functional food of the present invention are not particularly limited, and it is preferred to take the functional food in such an amount that the above-mentioned dose of the active component is generally achieved. For example, the present functional food may be taken continuously or intermittently before or after the symptoms of sleep disorder or the like caused by disorder of an endogenous melatonin secretion rhythm or a circadian rhythm are developed.

EXAMPLES

The present invention will now be explained in more detail with reference to Examples, which do not intend to limit the present invention.

Examples 1 and 2

Commercially available skim milk was dissolved in distilled water at a solid content of 9 mass %, subjected to high temperature pasteurization in an autoclave at 105° C. for 10 minutes, allowed to cool to the room temperature, inoculated with 3 mass % of a pre-cultured CM4 starter, and cultured at 37° C. for 24 hours, to thereby obtain fermented milk. This fermented milk was centrifuged at 12000 G for 20 minutes for removing the solids, to prepare fermented milk whey.

On the other hand, commercially available skin milk was dissolved in distilled water at a solid content of 9 mass %, subjected to high temperature pasteurization in an autoclave at 105° C. for 10 minutes, and allowed to cool to the room temperature. Lactic acid was added to increase the acidity to 2.2%. Then the product was centrifuged at 12000 G for 20 minutes for removing the solids, to prepare casein whey.

Each of the obtained fermented milk whey (Example 1) and casein whey (Example 2) was diluted with distilled water to 10 mass %, and used in the following animal test as a drinking water. As a control, distilled water without whey was also used in the test.

Fifty one male Wistar rats at 3 weeks of age were pre-bred for 1 week. During the pre-breeding, the rats were allowed free access to solid feed (trade name MF, manufactured by ORIENTAL YEAST CO., LTD.) and distilled water. The daily light-dark cycle during the pre-breeding was set such that the light cycle was from 8:00 to 20:00 and the dark cycle was for 12 hours after that. After the pre-breeding, the rats were divided into three groups of 17 animals each, i.e., Group (1) taking distilled water (control), Group (2) taking 10 mass % fermented milk whey (Example 1), and Group (3) taking 10 mass % casein whey (Example 2), and bred with free access to the respective drinks and solid feed for 1 month. After 1 month of breeding, 8 animals in each group was slaughtered at 12:00, and the remaining 9 animals in each group at 0:00, and the corpus pineale of each animal was taken out of the brain. 200 μl of 0.1 M perchloric acid was added, and the mixture was homogenized and centrifuged. The melatonin content in the resulting supernatant was measured, whereas the precipitate was collected for quantification of proteins.

The melatonin content was measured using Melatonin EIA Kit (trade name, manufactured by IBL Hamburg). The proteins were quantified by the Bradford method using Bio-Rad Protein Assay (trade name, manufactured by Bio-Rad) The results of the measurement of melatonin content at 12:00 are shown in FIG. 1, and those at 0:00 in FIG. 2. The statistical significance was determined by the student-newman-keuls test.

Figure 2:
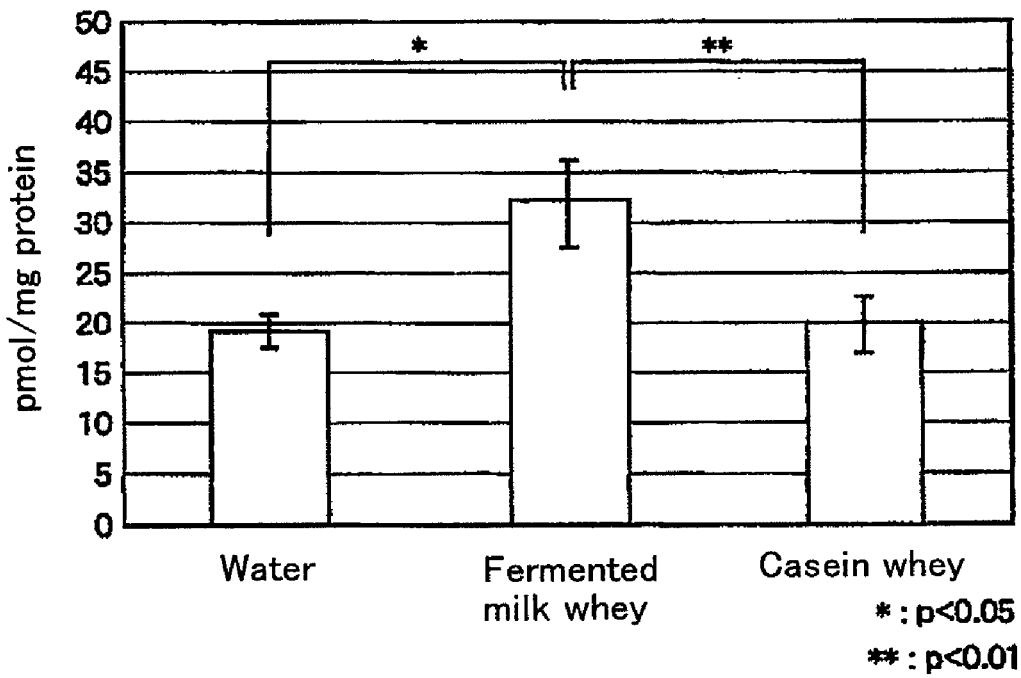
FIG. 2 is a graph illustrating the comparison among the groups of the melatonin concentration in the corpus pineale at 0:00 performed in Examples 1 and 2.

As seen from FIGS. 1 and 2, in Group (1) taking distilled water (control), the melatonin concentration was low at 12:00 and high at 0:00, showing the behavior of melatonin that is low in day time and high in night time. As seen from FIGS. 1 and 2, in Group (2) taking the fermented milk whey and Group (3) taking the casein whey, the melatonin concentration was lower at 12:00 and higher at 0:00, compared to those in Group (1) taking distilled water. Particularly, in Group (2) taking the fermented milk whey, the melatonin concentration at 12:00 was significantly lower than that in Group (1) taking distilled water (significance level $p<0.05$), and the melatonin concentration at 0:00 was significantly higher than that in Group (1) taking distilled water (significance level $p<0.05$) and that in Group (3) taking the casein whey (significance level $p<0.01$).

The above results suggest that intake of fermented milk whey or casein whey enhances the behavior of melatonin concentration that is low in day time and high in night time. In particular, the amplitude of enhancement was large when the fermented milk whey was taken, suggesting that the fermented milk whey has still stronger effect. That is, by taking fermented milk whey or casein whey, the endogenous melatonin secretion rhythm is phase-adjusted or the amplitude thereof is enhanced. The amplitude of enhancement is larger for fermented milk whey than for casein whey, which suggests that fermentation still enhances the effect.

Examples 3 and 4

Thirty three male Wistar rats at 3 weeks of age were pre-bred for 1 week. During the pre-breeding, the rats were allowed free access to solid feed (trade name MF, manufactured by ORIENTAL YEAST CO., LTD.) and distilled water. The daily light-dark cycle during the pre-breeding was set such that the light cycle was from 8:00 to 20:00 and the dark cycle was for 12 hours after that. After the pre-breeding, the rats were divided into three groups (1) to (3) of 11 animals each in the same way as in Examples 1 and 2, and bred with free access to the respective drinks and solid feed for 1 month. After 1 month of breeding, 5 animals in each group was slaughtered at 12:00, and the remaining 6 animals in each group at 0:00, and the corpus pineale of each animal was taken out of the brain. The NAT activity in the corpus pineale was measured by the method of Thomas et al.

Specifically, 100 ml of 0.25M calcium phosphate buffer (pH 7.5) containing 1.5 mM of acetyl CoA was added to the corpus pineale, and homogenized to prepare an enzyme solution. To 30 ml of the enzyme solution, 70 ml of 0.25 M calcium phosphate buffer containing 1.5 mM of acetyl CoA and 20 mM of tryptamine was added and reacted at 37° C. for 30 minutes, to which 1 ml of a toluene/isoamyl alcohol/1M HCl (99:0.66:0.33) solution was added. After stirring, the mixture was centrifuged at 500 G for 10 minutes, and 750 ml of the supernatant was evaporated in a centrifugal evaporator to obtain a dried product. 100 ml of a mobile phase (0.1 M citric acid, 0.1M sodium acetate, 35% methanol (pH 4.1)) was added and stirred, and the resulting solution was measured for N-acetyltryptamine by a high performance liquid chromatography with fluorescence detector. The measurement was performed at the excitation wavelength of 285 nm, detection wavelength of 360 nm, and flow rate of 1 ml/min, using a colum, Wakosil-II 5C18 RS (4.6 mm×150 mm). The proteins were quantified by the Bradford method against BSA standards.

Figure 3:
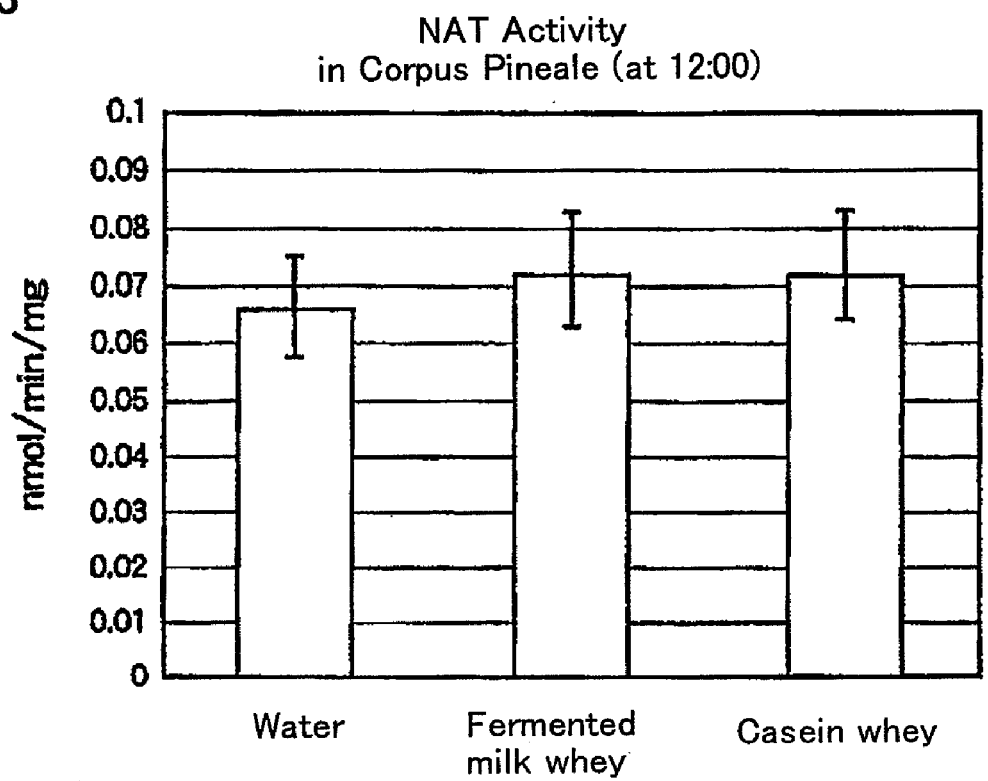
FIG. 3 is a graph illustrating the comparison among the groups of the NAT activity in the corpus pineale at 12:00 performed in Examples 3 and 4.
Figure 4:
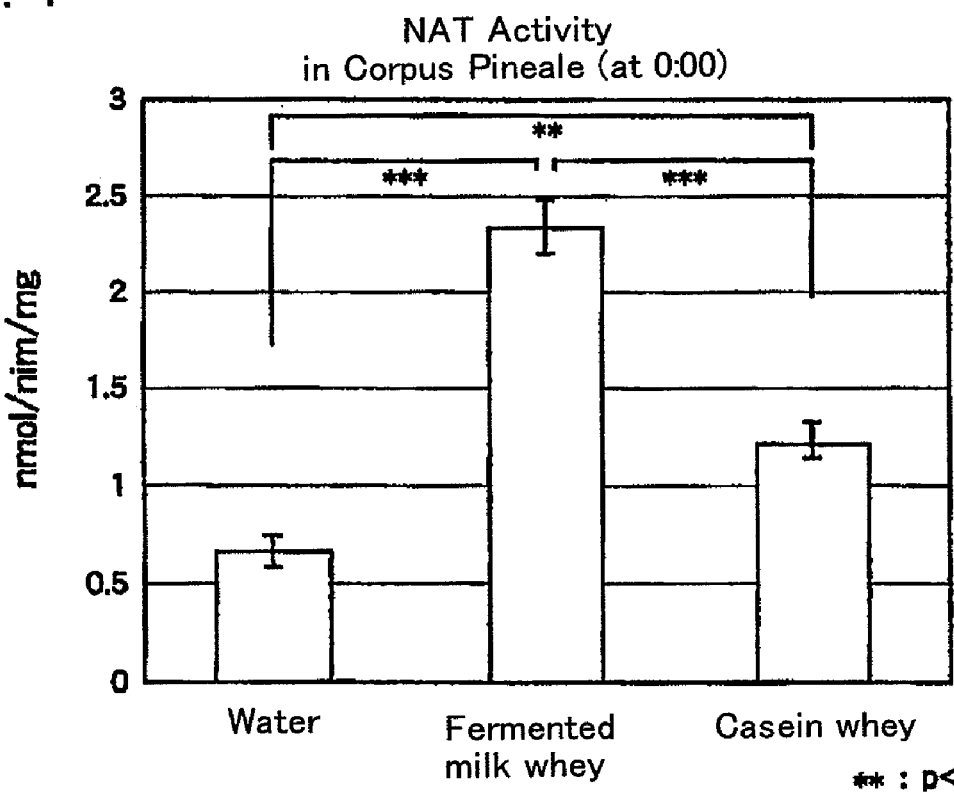
FIG. 4 is a graph illustrating the comparison among the groups of the NAT activity in the corpus pineale at 0:00 performed in Examples 3 and 4.

The results of measurement of the NAT activity at 12:00 are shown in FIG. 3, and those at 0:00 in FIG. 4. The statistical significance was determined by the student-newman-keuls test.

As seen from FIGS. 3 and 4, no difference in the NAT activity at 12:00 was observed among the groups, but at 0:00 the NAT activity in Group (2) taking the fermented milk whey (Example 3) was significantly higher than that in Group (1) taking distilled water (control) and that in Group (3) taking the casein whey (Example 4) (significance level $p<0.01$). Further, the NAT activity in Group (3) taking the casein whey was significantly higher than that in Group (1) taking distilled water (significance level $p<0.05$). Considering the fact that NAT is a rate-limiting enzyme in melatonin synthesis, it is confirmed from these results that NAT supports the change in melatonin concentration in the corpus pineale.

Prescription Example 1

90 mass % of fermented milk containing the fermented milk whey prepared in Example 1, 0.05 mass % of Aspartame (trade name, manufactured by AJINOMOTO K.K.) for drinkability, 0.05 mass % of Yoghurt Flavor cw-3186 (manufactured by T. HASEGAWA CO., LTD.) and 0.1 mass % each of Yoghurt Flavor DY 4449 and Sugar Flavor HASE SF-5531 (manufactured by T. HASEGAWA CO., LTD.) as flavoring agents, 0.5 mass % of a stabilizer, and 9.2 mass % of distilled water were mixed as starting materials. The mixture was homogenized and pasteurized at 90° C. The resulting product was hot-filled into brown bottles by 100 g, and pasteurized by heating at 80° C. for 10 minutes, to thereby obtain a fermented sour milk drink.

What is claimed is:
1. A method for phase-adjusting or enhancing the amplitude of endogenous melatonin secretion rhythm comprising orally administering to an animal in need thereof an effective amount of an agent comprising, as an active component, fermented milk whey, wherein the fermented milk whey is obtained by fermenting milk with lactic acid bacteria of the species *Lactobacillus helveticus* to obtain fermented milk; and removing solids from the obtained fermented milk by centrifugation.

2. The method for phase-adjusting or enhancing the amplitude of endogenous melatonin secretion rhythm according to claim 1, wherein said *Lactobacillus helveticus* is *Lactobacillus helveticus* CM4 (deposited at National Institute of Advanced Industrial Science and Technology, International Patent Organism Depositary under Accession Number FERM BP-6060).

3. A method for improving circadian rhythm comprising orally administering to an animal in need thereof an effective amount of an agent comprising, as an active component, fermented milk whey, wherein the fermented milk whey is obtained by fermenting milk with lactic acid bacteria of the species *Lactobacillus helveticus* to obtain fermented milk, and removing solids from the obtained fermented milk by centrifugation.

4. The method for improving circadian rhythm according to claim 3, wherein said *Lactobacillus helveticus* is *Lactobacillus helveticus* CM4 (deposited at National Institute of Advanced Industrial Science and Technology, International Patent Organism Depositary under Accession Number FERM BP-6060).

\* \* \* \* \*

UNITED STATES PATENT AND TRADEMARK OFFICE
CERTIFICATE OF CORRECTION

PATENT NO. : 8,067,034 B2 Page 1 of 1
APPLICATION NO. : 11/952839
DATED : November 29, 2011
INVENTOR(S) : Yoshinori Moriyama et al.

It is certified that error appears in the above-identified patent and that said Letters Patent is hereby corrected as shown below:

Title Page, Item (63) should read:

Related U.S. Application Data

(63) Continuation of application No. 10/599,446, now abandoned, which is a 371 of application No. PCT/JP2005/006244 filed on Mar. 31, 2005.

Signed and Sealed this
Twenty-fifth Day of September, 2012

David J. Kappos
*Director of the United States Patent and Trademark Office*